US012491295B2

(12) United States Patent
Gagel et al.

(10) Patent No.: US 12,491,295 B2
(45) Date of Patent: Dec. 9, 2025

(54) EXTRACORPOREAL BLOOD TREATMENT DEVICE

(71) Applicant: FRESENIUS MEDICAL CARE DEUTSCHLAND GMBH, Bad Homburg (DE)

(72) Inventors: Alfred Gagel, Litzendorf (DE); Burkard Keller, Wuerzburg (DE); Peter Kloeffel, Nuedlingen (DE); Martin Thys, Grettstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 489 days.

(21) Appl. No.: 17/920,406

(22) PCT Filed: Apr. 21, 2021

(86) PCT No.: PCT/EP2021/060316

§ 371 (c)(1),
(2) Date: Oct. 21, 2022

(87) PCT Pub. No.: WO2021/219451

PCT Pub. Date: Nov. 4, 2021

(65) Prior Publication Data

US 2023/0158217 A1 May 25, 2023

(30) Foreign Application Priority Data

Apr. 30, 2020 (DE) ..................... 10 2020 111 764.7

(51) Int. Cl.
*A61M 1/16* (2006.01)
*A61M 1/36* (2006.01)

(52) U.S. Cl.
CPC .......... *A61M 1/1601* (2014.02); *A61M 1/165* (2014.02); *A61M 1/3644* (2014.02); *A61M 2205/3331* (2013.01)

(58) Field of Classification Search
CPC .. A61M 1/1601; A61M 1/165; A61M 1/3644; A61M 2205/3331
See application file for complete search history.

(56) References Cited

U.S. PATENT DOCUMENTS

| | | | | |
|---|---|---|---|---|
| 2013/0026098 A1* | 1/2013 | Haecker | .................. | A61M 1/16 210/97 |
| 2013/0284671 A1 | 10/2013 | Wiesen | | |
| 2019/0125950 A1 | 5/2019 | Noack | | |

FOREIGN PATENT DOCUMENTS

| | | |
|---|---|---|
| DE | 102010032154 A1 | 1/2012 |

OTHER PUBLICATIONS

International Search Report and Written Opinion issued in corresponding International Patent Application No. PCT/EP2021/060316 (with English translation of International Search Report) mailed Jul. 29, 2021 (15 pages).

(Continued)

*Primary Examiner* — John Kim
(74) *Attorney, Agent, or Firm* — Kilyk & Bowersox, P.L.L.C.

(57) ABSTRACT

The invention relates to an extracorporeal blood treatment apparatus comprising a blood treatment unit 1 that is divided by a semipermeable membrane 2 into a first compartment 3, which is part of a fluid system II, and a second compartment 4, which is part of an extracorporeal blood circuit I. The invention also relates to a method for operating a blood treatment apparatus of this kind. The blood treatment apparatus according to the invention has a pressure-based checking device 32 which interacts with the control unit 31 for a valve device 21 and is designed such that a fluid connection (Continued)

Figure 1:
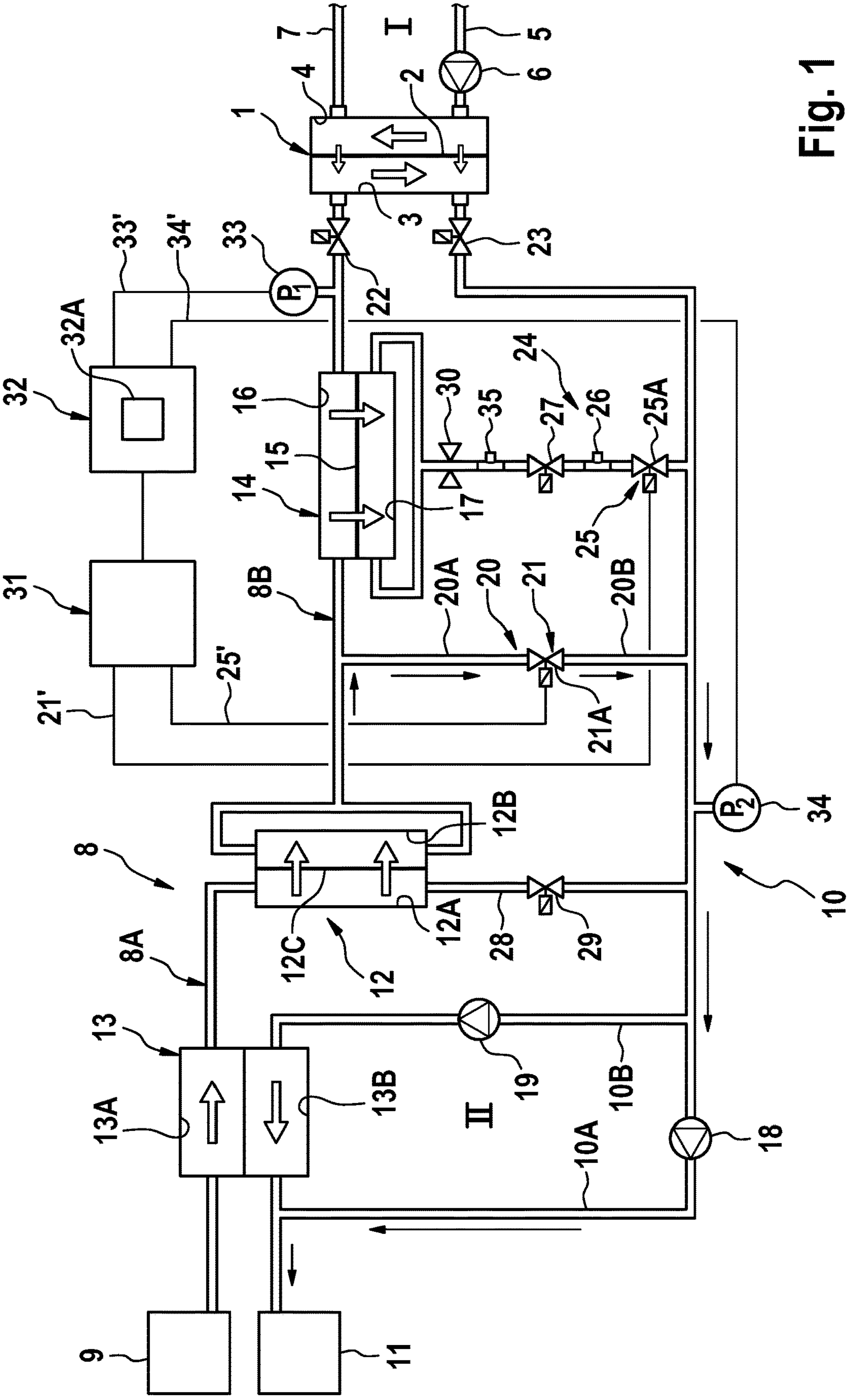

between an upstream portion 20A and a downstream portion 20B of a flow path 20 for a special operating mode can only be established if the pressure-based checking device 32 detects an operating state in which it is ensured that fluid in the flow path 20 for a special operating mode flows towards a flow path 10 leading to a drain 11. This ensures that the fluid in question can only flow into the flow path 10 that leads to the drain 11, and cannot get into another flow path 8 in which fresh treatment fluid is located.

8 Claims, 2 Drawing Sheets

(56) References Cited

OTHER PUBLICATIONS

International Preliminary Report on Patentability issued in corresponding International Patent Application No. PCT/EP2021/060316 issued Oct. 27, 2022 (English translation) (9 pages).

* cited by examiner

EXTRACORPOREAL BLOOD TREATMENT DEVICE

This application is a National Stage Application of PCT/EP2021/060316, filed Apr. 21, 2021, which claims priority to German Patent Application No. 10 2020 111 764.7, filed Apr. 30, 2020.

The invention relates to an extracorporeal blood treatment apparatus comprising a blood treatment unit that is divided by a semipermeable membrane into a first compartment, which is part of a fluid system, and a second compartment, which is part of an extracorporeal blood circuit. The invention also relates to a method for operating a blood treatment apparatus of this kind.

Known dialysis apparatuses comprise an extracorporeal blood circuit and a dialysis fluid system. The dialysis fluid system comprises a dialysis fluid supply line, which leads from a dialysis fluid source to the dialysis fluid chamber of a dialyser, and a dialysis fluid discharge line, which leads from the dialysis fluid chamber of the dialyser to a drain. The extracorporeal blood circuit comprises an arterial blood line, which leads from an arterial puncture site of the patient to the blood chamber, and a venous blood line, which leads from the blood chamber to a venous puncture site of the patient. While the dialysis fluid flows through the dialysis fluid chamber of the dialyser, there is a transfer of mass between the blood chamber and the dialysis fluid chamber via the semipermeable membrane of the dialyser.

The fluid system of known extracorporeal blood treatment apparatuses, for example dialysis apparatuses, is generally constructed such that a fresh medical treatment fluid, for example dialysis fluid, flows into the first compartment of the blood treatment unit and used treatment fluid flows out of the first compartment of the blood treatment unit into a drain at a predetermined flow rate. The fluid system of known blood treatment apparatuses therefore generally comprises a first flow path that has at least one fluid line and is designed as a flow path for supplying a fresh treatment fluid from a fluid source to the first compartment of the blood treatment unit, and a second flow path that has at least one fluid line and is designed as a flow path for discharging a used treatment fluid from the first compartment of the blood treatment unit to a drain. In order to reduce the risk of contamination, the first and the second flow path of known blood treatment apparatuses are separate from one another.

The fluid system of known blood treatment apparatuses generally has additional flow paths which are each required for a special operating mode. These special operating modes include, for example, filling the blood treatment apparatus with a cleaning agent and/or disinfectant or preparing the blood tube system for blood treatment. Creating a flow connection between the first and the second flow path and thereby bypassing the blood treatment unit, in preparation for blood treatment or during blood treatment in the event of a fault, is also a special operating mode.

To control the flow of fluid, the fluid systems of known blood treatment apparatuses contain valve devices, which can comprise one or more shut-off members, and a control unit for actuating the valve device such that the valve device assumes one operating position for one operating mode and another operating position for another operating mode.

The flow paths for the special operating modes comprise an upstream portion upstream of a valve device that has at least one valve, and a downstream portion downstream of the valve device, the valve device being designed such that a fluid connection is established between the upstream portion and the downstream portion of the flow path in a first operating position of the valve device and the fluid connection is interrupted in a second operating position of the valve device. For individual operating modes, it may be necessary for the downstream portion of the flow path, for a special operating mode, to be in flow connection with the second flow path, so that a fluid, for example dialysis fluid, can flow directly from the upstream portion into the drain via the second flow path if the flow connection in the flow path is not interrupted.

A dialysis apparatus comprising two separate flow paths in which fresh and used dialysis fluid flows during blood treatment is known from EP 2 844 313 B1, for example. The fluid system of the dialysis apparatus has a valve device comprising a plurality of shut-off members in order to carry out a flushing process.

The object of the invention is to provide an additional safety measure in order to further reduce the risk of contaminating the blood treatment apparatus as a result of a used fluid flowing into a fresh fluid.

According to the invention, this object is achieved by the features of the independent claims. The dependent claims relate to preferred embodiments of the invention.

The blood treatment apparatus according to the invention has a valve device which is provided in a flow path for a special operating mode. The valve device is designed such that a fluid connection is established between an upstream portion and a downstream portion of the flow path for a special operating mode in a first operating position of the valve device and the fluid connection is interrupted in a second operating position of the valve device. The blood treatment apparatus also has a pressure-based checking device which interacts with a control unit for actuating the valve device, and is designed such that a fluid connection between the upstream portion and the downstream portion of the flow path for a special operating mode can only be established if the pressure-based checking device detects an operating state in which it is ensured that fluid in the flow path for a special operating mode flows towards a flow path leading to a drain. This ensures that the fluid in question can only flow into the flow path that leads to the drain, and cannot get into another flow path in which fresh treatment fluid is located.

For monitoring the flow direction according to the invention, it is fundamentally irrelevant in which fluid line fluid flows in the special operating mode or which fluid it is.

In a preferred embodiment, the pressure-based checking device comprises an upstream pressure gauge for measuring the upstream pressure in the upstream portion of the flow path for a special operating mode, a downstream pressure gauge for measuring the downstream pressure in the downstream portion of the flow path and an evaluation unit that receives the measurement signals from the upstream and the downstream pressure gauge. The evaluation unit is configured such that the upstream pressure is compared with the downstream pressure and, if the upstream pressure is higher than the downstream pressure, this indicates an operating state in which it is ensured that fluid flows towards the second flow path.

The control unit and/or evaluation unit can be part of the central control and arithmetic unit of the blood treatment apparatus. The pressure can be measured by a pressure gauge which is arranged on the upstream or downstream portion of the flow path for the special operating mode, or by a pressure gauge which is arranged on a fluid line that is fluidically connected to the portion in question. Pressure gauges which are already provided in conventional blood treatment apparatuses for monitoring blood treatment are preferably used.

If a faulty operating state is indicated, a wide variety of measures can be taken. For example, an acoustic, visual or tactile alarm can be emitted to alert medical staff and respond accordingly.

The control unit of the valve device or the central control and arithmetic unit of the blood treatment apparatus can be configured such that, after receiving a signal from the evaluation unit that signals a faulty operating state, measures are introduced or method steps are carried out which result in correct pressure conditions.

In another embodiment, the pressure-based checking device generates an enabling signal for the control unit, the control unit being configured such that the valve device is only actuated such that the valve device assumes the first operating position if the control unit receives a control signal for switching to the special operating mode and the enabling signal. Consequently, the flow connection can only be established by means of the valve device if it is ensured that the fluid cannot get into the part of the fluid system in which the fresh treatment fluid is located.

Another embodiment requires the fluid system of the blood treatment apparatus to have a special structure in which the first flow path comprises a first filter that is divided into a first filter chamber and a second filter chamber by a semipermeable membrane. This filter can act as a sterile filter for the fresh dialysis fluid. An upstream portion of the first flow path connects the fluid source to the first filter chamber of the filter, and a downstream portion of the first flow path connects the second filter chamber of the filter to an inlet of the first compartment of the blood treatment unit. In this embodiment, the upstream portion of the flow path for the special operating mode can be a line portion that is in fluid connection with the downstream portion of the first flow path. Since the downstream portion of the flow path for a special operating mode is in flow connection with the second flow path and thus with the drain, for the special operating state a flow connection can be established downstream of the sterile filter between the first flow path for fresh treatment fluid and the second flow path for used treatment fluid, thereby bypassing the blood treatment unit.

In this embodiment, the first pressure gauge can be arranged on the downstream part of the first flow path, and the second pressure gauge can be arranged on the second flow path. It may be expedient not to arrange the pressure gauges directly on the upstream and downstream portions of the flow path for a special operating mode if pressure gauges are already provided on other fluid lines in the blood treatment apparatus for monitoring the pressure.

In another embodiment, in which the extracorporeal blood circuit comprises a venous blood line and an arterial blood line, the upstream portion of the flow path for a special operating mode is a line portion of the venous blood line or a line portion that is in fluid connection with the venous blood line. In this embodiment, the monitoring of the flow direction only allows fluid to flow from the venous blood line into the drain, and the first pressure gauge can be arranged on the venous blood line and the second pressure gauge can be arranged on the second flow path.

In the method according to the invention for operating an extracorporeal blood treatment apparatus, the upstream pressure in the upstream portion and the downstream pressure in the downstream portion of a flow path for a special operating state are measured before a flow connection is established between an upstream portion of the flow path for a special operating state and a downstream portion of the flow path for a special operating state which is in flow connection with the second flow path. The flow connection between the upstream and the downstream portion of the flow path for a special operating state is only established if the upstream pressure is higher than the downstream pressure.

Figure 2:
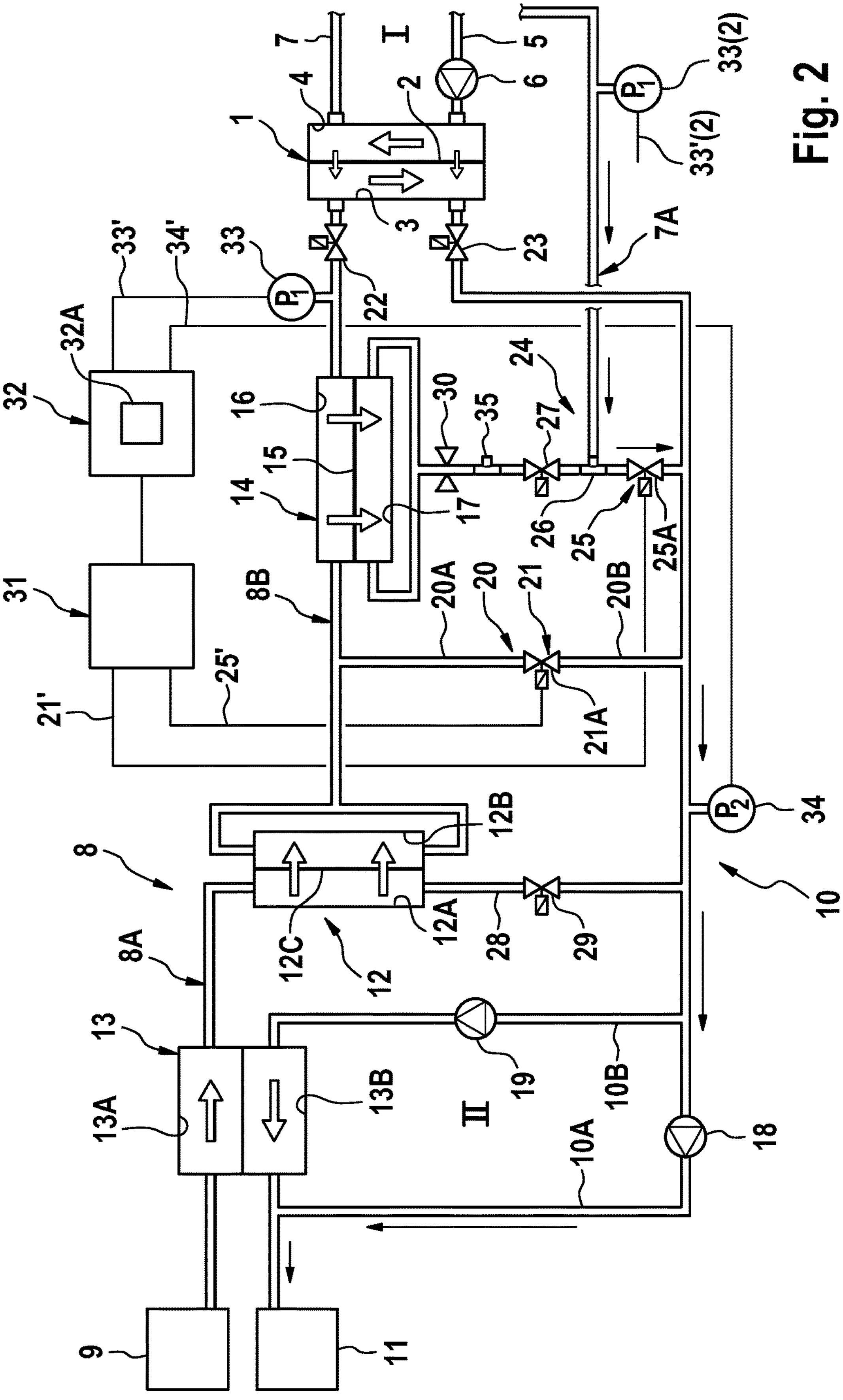

Two embodiments of the invention are explained in detail below with reference to the drawings, in which:

FIG. 1 is a highly simplified schematic view of an embodiment of the blood treatment apparatus according to the invention in which the flow direction of a fluid is monitored for controlling a first valve device; and FIG. 2 is a highly simplified schematic view of an embodiment of the blood treatment apparatus according to the invention in which the flow direction of a fluid is monitored for controlling a second valve device.

The blood treatment apparatus, in particular a hemo(dia) filtration apparatus, is equipped for operation with a blood treatment unit 1, in particular a dialyser, which is divided into a first compartment 3, in particular a dialysis fluid chamber, and a second compartment 4, in particular a blood chamber, by a semipermeable membrane 2.

A blood supply line 5, into which a blood pump 6 is connected, leads to the inlet 4*a* of the blood chamber 4, while a blood return line 7 leads out from the outlet 4*b* of the blood chamber 4. Together with the blood chamber 4, the blood supply line and blood discharge line 5, 7 form the extracorporeal blood circuit I of the blood treatment apparatus. The fluid system II of the blood treatment apparatus is described below. The blood supply and discharge line 5, 7 are part of a tube system that is connected to the blood treatment apparatus.

The fluid system II of the blood treatment apparatus, in particular the dialysis fluid system, comprises a dialysis fluid supply line 8 which leads from a dialysis fluid source 9 to an inlet 3*a* of the dialysis fluid chamber 3, and a dialysis fluid discharge line 10 which leads out from an outlet 3*b* of the dialysis fluid chamber 3 and leads to a drain 11. The dialysis fluid supply line 8 has a first portion 8A that leads from the dialysis fluid source 9 to the first filter chamber 12A of a first sterile filter 12, which is divided into the first filter chamber 12A and a second filter chamber 12B by a semipermeable membrane 12C. One chamber 13A of a balancing device 13 is connected into the first portion 8A of the dialysis fluid supply line 8. The second portion 8B of the dialysis fluid supply line 8, which leads to the dialysis fluid chamber 3, leads out from the second filter chamber 12B of the first sterile filter 12.

In order to obtain a substituate from the dialysis fluid, the hemo(dia)filtration apparatus can comprise a second sterile filter 14, which is divided into a first filter chamber 16 and a second filter chamber 17 by a semipermeable membrane 15. The first filter chamber 16 of the second sterile filter 14 is connected into the second portion 8B of the dialysis fluid supply line 8. The substituate line is not shown in FIG. 1.

The dialysis fluid discharge line 10 divides into two portions 10A and 10B which lead to the drain 11. A dialysis fluid pump 18 is connected into the first portion 10A, while an ultrafiltrate pump 19 is connected into the second portion 10B. In addition, the other chamber 13B of the balancing device 13 is connected into the second portion 10B.

During blood treatment, fresh dialysis fluid flows from the dialysis fluid source 9 into the dialysis fluid chamber 3 and used dialysis fluid flows out of the dialysis fluid chamber 3 into the drain 11. The dialysis fluid supply line represents a first flow path 8 in which fresh dialysis fluid flows from the dialysis fluid source 9 to the dialysis fluid chamber 3, while the dialysis fluid discharge line represents a second flow path 10 in which used dialysis fluid flows from the dialysis fluid chamber 3 to the drain 11. The flow paths form all the portions of the relevant lines, including the components connected into the lines.

A bypass line 20 which leads to the dialysis fluid discharge line 10 branches off the second portion 8B of the dialysis fluid supply line 8 downstream of the second filter chamber 12B of the first sterile filter 11. A first valve device 21, which has an electromagnetically activatable shut-off member 21A, is connected into the second bypass line 20. The bypass line represent a flow path 20 which is provided for a special operating mode. This operating mode can, for example, be a malfunction, e.g. detection of an incorrect composition of the dialysis fluid, which can be detected by measuring conductivity. If this malfunction occurs, the shut-off member 21A of the first valve device 21 is opened so that the dialysis fluid can be guided into the drain 11 while bypassing the dialyser 3. To isolate the dialyser 3, a shut-off member 22 is provided upstream and a shut-off member 23 is provided downstream of the dialysis fluid chamber 3.

The line portion of the bypass line 20 that is connected to the dialysis fluid supply line 8 will hereinafter be referred to as the upstream portion 20A, and the line portion of the bypass line 20 that is connected to the dialysis fluid discharge line 10 will be referred to as the downstream portion of the flow path 20 for a special operating mode.

The second filter chamber of the second sterile filter 14 is connected to the dialysis fluid discharge line 10 via a connecting line 24. A second valve device 25 which has an electromagnetically activatable shut-off member 25A is connected into the connecting line 10. A connection piece 26 (port) to which the venous blood line 7A (FIG. 2) can be connected in order to flush the venous blood line 7A is located upstream of this shut-off member 25A. A shut-off member 27 which is closed for the flushing process is provided upstream of the connection piece 26. Flushing the venous blood line 7A is another example of a special operating mode which will be explained in more detail with reference to FIG. 2.

Additional lines, shut-off members or connection pieces (ports) can also be provided, but are not important for understanding the invention: for example the line denoted by reference sign 28 and the shut-off members 29, 30 or the connection piece 35 (port).

The blood treatment apparatus has a control unit 31 which is configured such that the shut-off members 21A and 25A of the first and the second valve device 21, 25, respectively, can be opened or closed. The control lines for the electromagnetically activatable shut-off members 21A and 25A of the first and the second valve device 21, 25, respectively, are denoted by reference signs 21', 25' in FIGS. 1 and 2. The control unit 31 can also actuate the other shut-off members.

The blood treatment apparatus has a checking device 32 which comprises an evaluation unit 32A that receives the measurement signal from a first pressure gauge 33 and the measurement signal from a second pressure gauge 34.

In the embodiment shown in FIG. 1, the first pressure gauge 33 is arranged on the downstream portion 8B of the dialysis fluid supply line 8 and measures the pressure $P_1$ in this line portion, while the second pressure gauge 34 is arranged on the dialysis fluid discharge line 10 upstream of the dialysis fluid pump 18 and the ultrafiltrate pump 19 and measures the pressure $P_2$ in this line portion. The two pressure gauges 33, 34 are connected to the checking device 32 via signal lines 33', 34'.

The first and the second shut-off member 21A, 25B are closed during blood treatment. If a special operating mode is specified, the control unit 31 receives a control signal to open the first or second shut-off member 21A, 25B. In the present embodiment, it is assumed that the control unit 31 receives a control signal to open the first or second shut-off member from a central control and arithmetic unit (not shown) of the blood treatment apparatus, which unit controls the preparation of the blood treatment apparatus for blood treatment and the blood treatment itself.

The evaluation unit 32A calculates the difference between the pressure $P_1$ measured by the first pressure gauge 33 and the pressure $P_2$ measured by the second pressure gauge 34 and generates an enabling signal received by the control unit 31 if the difference is greater than 0, i.e. $P_1>P_2$. The control unit 31 only opens the first or second shut-off member 21A or 25A if it receives both the corresponding control signal for the first or second shut-off member from the central control and arithmetic unit and the enabling signal from the evaluation unit 32A.

If the control unit 31 receives the corresponding control signal for the "bypass" operating mode, a flow connection is only established between the upstream and downstream portion 20A, 20B of the flow path 20 for this special operating mode if the pressure $P_1>P_2$, so that it is ensured that fresh dialysis fluid flows from the first flow path 8 into the second flow pad 10 and thus into the drain 11. If the pressure $P_1<P_2$, the enabling signal is not generated, so that there is no danger that used dialysis fluid from the second flow path 10 will get into the first flow path 8 for fresh dialysis fluid. In FIG. 1, the flow direction for the dialysis fluid when the shut-off member 21A of the first valve device 21 is open is indicated by arrows. Other operating states can also be taken into account for the bypass operation. For example, no unphysiological dialysis fluid may get into the dialyser 1. If $P_1<P_2$, suitable measures can be taken to increase the pressure $P_1$ in the first flow path 8. These measures can involve closing the shut-off member 22 in the first flow path 8 upstream of the dialysis fluid chamber 3 of the dialyser 1. If the shut-off member 22 has been closed, so that $P_1>P_2$, the shut-off member 21 can be opened. The shut-off member 29 can also be opened instead of the shut-off member 21.

FIG. 2 shows the extracorporeal blood treatment apparatus from FIG. 1 with the venous tube line 7A connected to the connection piece 26, in order to prepare for the blood treatment, such that a flushing fluid can flow through the venous blood line 7A to the drain 11 when the shut-off member 25A of the second valve device 25 is open. To flush the venous blood line 7A, the shut-off member 27 upstream of the shut-off member 25A of the second valve device 25 is closed. In this embodiment, the first pressure gauge is a pressure gauge 33(2) which is arranged on the venous blood line 7A and measures the pressure $P_1$ in this line upstream of the shut-off member 25A of the second valve device 25. The second pressure gauge, as in the first embodiment from FIG. 1, is a pressure gauge 34 which is arranged on the dialysis fluid discharge line 10 and measures the pressure $P_2$ in this line.

If the venous blood line 7A is connected to the connection piece 26 and the control unit 31 receives the corresponding control signal for the special operating mode "flushing the blood line", the shut-off member 25A of the second valve device 25 is only opened if the pressure $P_1>P_2$, so that it is ensured that flushing fluid can only flow towards the second flow path 10. In FIG. 2, the flow direction for the flushing fluid when the shut-off member 25A of the second valve device 25 is open is indicated by arrows.

Only one of the two embodiments may be implemented in a blood treatment apparatus. However, it is also possible for both embodiments to be implemented. The flow direction can also be monitored in other "critical flow paths" by means of the checking device according to the invention. In this sense, the two operating modes described should be understood only as one embodiment for a "critical flow path".

The invention claimed is:

1. An extracorporeal blood treatment apparatus designed for connection to a blood treatment unit that is divided by a semipermeable membrane into a first compartment, which is part of a fluid system, and a second compartment, which is part of an extracorporeal blood circuit, the fluid system comprising a first flow path that has at least one fluid line and is designed as a flow path for supplying a fresh treatment fluid from a fluid source to the first compartment of the blood treatment unit, and comprising a second flow path that has at least one fluid line and is designed as a flow path for discharging a used treatment fluid from the first compartment of the blood treatment unit to a drain, and at least one additional flow path that has at least one fluid line being provided for a special operating mode, said at least one additional flow path having an upstream portion which is upstream of a valve device that has at least one shut-off member, and a downstream portion which is downstream of the valve device and is in fluid connection with the second flow path, the valve device being designed such that a fluid connection is established between the upstream portion and the downstream portion of the at least one additional flow path for the special operating mode in a first operating position of the valve device and the fluid connection is interrupted in a second operating position of the valve device, a control unit for actuating the valve device such that the valve device assumes the first operating position for the special operating mode and the second operating position for another operating mode, wherein a pressure-based checking device is provided which interacts with the control unit and is designed such that a fluid connection between the upstream portion and the downstream portion of the at least one additional flow path for the special operating mode is only established when the pressure-based checking device detects an operating state in which it is ensured that fluid in the at least one additional flow path for the special operating mode flows towards the second flow path.

2. The extracorporeal blood treatment apparatus according to claim 1, wherein the pressure-based checking device comprises an upstream pressure gauge for measuring the upstream pressure in the upstream portion of the at least one additional flow path for the special operating mode, a downstream pressure gauge for measuring the downstream pressure in the downstream portion of the at least one additional flow path for the special operating mode, and an evaluation unit which receives the measurement signals from the upstream and the downstream pressure gauge and is configured such that the upstream pressure is compared with the downstream pressure and, if the upstream pressure is higher than the downstream pressure, this indicates an operating state in which it is ensured that fluid flows towards the second flow path.

3. The extracorporeal blood treatment apparatus according to claim 1, wherein the pressure-based checking device is configured such that the pressure-based checking device generates an enabling signal for the control unit, the control unit being configured such that the valve device is only actuated such that the valve device assumes the first operating position if the control unit receives a control signal for switching to the special operating mode and the enabling signal from the pressure-based checking device.

4. The extracorporeal blood treatment apparatus according to claim 1, wherein the first flow path comprises a first filter which is divided into a first filter chamber and a second filter chamber by a semipermeable membrane, an upstream portion of the first flow path connecting the fluid source to the first filter chamber of the filter and a downstream portion of the first flow path connecting the second filter chamber of the filter to an inlet of the first compartment of the blood treatment unit, and the upstream portion of the at least one additional flow path for the special operating mode being a line portion which is in fluid connection with the downstream portion of the first flow path.

5. The extracorporeal blood treatment apparatus according to claim 4, wherein the first pressure gauge is arranged on the downstream part of the first flow path, and the second pressure gauge is arranged on the second flow path.

6. The extracorporeal blood treatment apparatus according to claim 1, wherein that the extracorporeal blood circuit comprises an arterial blood line and a venous blood line, the upstream portion of the at least one additional flow path for the special operating mode being a line portion of the venous blood line or a line portion which is in fluid connection with the venous blood line.

7. The extracorporeal blood treatment apparatus according to claim 6, wherein the first pressure gauge is arranged on the venous blood line, and the second pressure gauge is arranged on the second flow path.

8. The extracorporeal blood treatment apparatus according to claim 1, wherein the blood treatment unit is a dialyser which is divided into a dialysis fluid chamber and a blood chamber by the semipermeable membrane.

* * * * *